United States Patent
Verhagen

(10) Patent No.: US 7,291,837 B2
(45) Date of Patent: Nov. 6, 2007

(54) APPARATUS AND METHOD FOR PREPARING SAMPLES FOR RADIOCARBON DATING

(76) Inventor: Balthazar T. Verhagen, 28 Eden Road, Bramley, Johannesburg 2090 (ZA)

( * ) Notice: Subject to any disclaimer, the term of this patent is extended or adjusted under 35 U.S.C. 154(b) by 57 days.

(21) Appl. No.: 10/924,672

(22) Filed: Aug. 23, 2004

(65) Prior Publication Data

US 2006/0038124 A1 Feb. 23, 2006

(51) Int. Cl.
*G01N 1/22* (2006.01)
(52) U.S. Cl. .......................... 250/304; 436/59; 422/83
(58) Field of Classification Search ................. 250/304
See application file for complete search history.

(56) References Cited

U.S. PATENT DOCUMENTS

| | | | | |
|---|---|---|---|---|
| 3,050,372 A | * | 8/1962 | Scott ........................... | 436/144 |
| 3,830,628 A | * | 8/1974 | Kaartinen .................... | 436/59 |
| 3,944,471 A | * | 3/1976 | Waters ........................ | 435/35 |
| 4,019,864 A | * | 4/1977 | Saito et al. .................. | 422/83 |
| 5,402,834 A | * | 4/1995 | Levin et al. ................. | 141/83 |

OTHER PUBLICATIONS

Thomson,J. Sample Preparation and Counting of Biological Samples, Packard Instrument Application Note AN9002-CSR, 1999.*

Thomson,J. Sample Preparation and Counting of Biological Samples, Packard Instrument Application Note AN9002-CSR, 1999.*

Leaney, et al., New Developments For The Direct CO, Absorption Method For Radiocarbon Analysis, Quarternary Geochronology/Quarternary Science Review, 1994, pp. 171-178, vol. 13, Elsevier Science Ltd., Great Britain.

Qureshi et al., The $CO_2$ absorption method as an alternative to benzene synthesis method for $^{14}C$ dating, Applied Geochemistry, 1989, pp. 625-633, vol. 4, Pergamons Press, Great Britain.

Aravena et al., New Possibilities for $^{14}C$ Measurements By Liquid Counting, Radiocarbon, 1989, pp. 387-392, vol. 31, No. 3, Geological Survey of Canada, Canada.

* cited by examiner

*Primary Examiner*—Nikita Wells
*Assistant Examiner*—Phillip Johnston
(74) *Attorney, Agent, or Firm*—Fulwider Patton LLP

(57) ABSTRACT

The invention provides a method and apparatus for preparing samples of carbon dioxide with a $^{14}C$ content for analysis in liquid scintillation counting equipment, the sample being of a known mass and being introduced into and substantially wholly absorbed into an absorption "cocktail", absorption being completed at a stage before saturation of the absorbent occurs. The absorbent is contained in a vial which, when absorption has been completed, is transferred into the scintillation counting equipment without intermediate transfer of the contents.

26 Claims, 3 Drawing Sheets

APPARATUS AND METHOD FOR PREPARING SAMPLES FOR RADIOCARBON DATING

FIELD OF THE INVENTION

This invention relates to the preparation of samples for use in laboratory procedures for radiocarbon dating and similar procedures that rely on the radioactive characteristics of the radioactive isotope, radiocarbon, or carbon-14 ($^{14}C$). The invention provides a method and apparatus for preparing samples containing carbon with a $^{14}C$ content for insertion into standard liquid scintillation equipment, where radioactivity associated with the carbon is detected and measured. From the measurements, determinations such as the age of the sample can be made.

BACKGROUND OF THE INVENTION

The radioactive properties of $^{14}C$ are well known and have given rise to technologies that include the technology of radiocarbon dating. This technology is widely practiced on a laboratory scale, particularly to determine the age of specimens of interest. The results are typically expressed as "percent modem carbon" or pMC, the percentage of the measured activity in the sample to that in a standard, based on the activity in wood grown in the year 1850, i.e. at the onset of the industrial revolution. The pMC value is then interpreted in terms of the age of the sample, generally measurable by the use of this technology to a period some tens of thousands of years from the time of measurement, usually expressed as a time before the present (BP).

Interest in radiocarbon techniques goes considerably beyond academic curiosity and many practical applications now exist. Among them is their use in the discipline of isotope hydrology. Radiocarbon, produced in the atmosphere, enters the biosphere through photosynthesis. Carbon dioxide, generated by biological activity in the soil, dissolves in infiltrating rain water to become part of the dissolved inorganic carbon in ground water. The decay of radiocarbon in this partially closed system gives a measure of the residence time, or "age" of ground water. This is unique information for hydrologists studying the dynamics of ground water movement.

Initially, when the radiocarbon element $^{14}C$ was discovered in the environment in the middle of the previous century, its presence was quantified by gas proportional counting. In this technique, a gas is produced from the carbon-containing sample which is introduced into a metal cylinder with a very fine wire along its axis, insulated from the cylinder, to which a high voltage is applied. Electric charges produced by radiation, such as from the decay of $^{14}C$, are attracted to the wire, producing impulses which can be recorded, or "counted." Some time later the technique of liquid scintillation counting was developed. This involves the use of sensitive photomultipliers to detect and measure small light emissions that follow the excitement of a liquid scintillator by the energy deposited by ionizing radiation, such as occurs in samples containing radiocarbon when atoms of $^{14}C$ decay by beta-radiation (that is, nuclear electron radiation) to nitrogen-14.

The liquid scintillation counting technique has been developed to a high degree of sophistication using modem computer technology. State-of-the-art, automated scintillation spectrometers are now marketed, vying in their sensitivity and accuracy with the classic, but cumbersome and labor-intensive, technique of gas counting.

The preparation of samples for use with liquid scintillation equipment is relatively time-consuming and tedious, involving numerous discrete steps, some of which call for manual intervention at various points. Although some of this work is repetitive and does not call for particularly skilled personnel to be involved, it is nevertheless precise and meticulous work.

Liquid scintillation counting relies on the use of a "cocktail" of organic substances that can undergo molecular excitation by absorbing energy deposited in the material by ionization caused by nuclear radiation, transferring this energy to a material which releases it as photons or quanta of light. Until the late 1980's carbon samples with environmental levels of radiocarbon were introduced into such a cocktail through the synthesis of benzene. This is an involved and relatively expensive process.

However, in the late 1980's an absorption technique, previously used for small, high-activity tracer samples, was adapted by Aravena et al. to environmental samples and is described in their paper entitled, "New Possiblities for $^{14}C$ Measurements by Liquid Scintillation Counting," in Radiocarbon, Vol 31, No. 3, 1989, pp. 387-393. This method was described in greater detail by Qureshi et al. in a paper, "The $CO_2$ absorption method as an alternative to benzene synthesis method for $^{14}C$ dating," in Applied Geochemistry, Vol 4, pp. 625-633, 1989. The latter reference describes how the $CO_2$ produced by appropriate processes from the carbon-containing samples and suitably purified, may be bubbled from a supply vessel through a mixture of a scintillation cocktail and an alkaline absorbant which binds the $CO_2$ in the form of a soluble carbamate. Using this method, in order to load an adequate amount of $CO_2$ into the cocktail, the bubbling process is continued until the cocktail is saturated, i.e. until the rate of absorption drops to zero. The mass of CO2 actually absorbed is determined by measuring the weight of the cocktail before and after the absorption process.

The method generally described in the aforementioned references has the advantage of much greater simplicity and is less time-consuming than the earlier benzene method. Although a considerably smaller amount of $CO_2$ is accommodated in the counting cocktail, implying less sensitivity, it is still useful for a variety of applications in which high precision is not required, such as hydrology. Nevertheless, shortcomings have been noted. Not all the gaseous $CO_2$ bubbling through the absorbent cocktail is immediately bound with the absorbent, and some of the $CO_2$ is allowed to flow to waste. As a result, substantially more $CO_2$, approximately 20%, has to be produced than can be accommodated in the liquid absorbent. Furthermore, as the pressure in the $CO_2$ supply vessel drops, nitrogen must be added as carrier gas to maintain the pressure. Conditions have to be kept constant in order to ensure the same saturation conditions between different preparations. Even so, the degree of saturation ultimately achieved has to be established by carefully measuring the sample weight before and after each run, because the amount of $CO_2$ absorbed under the same conditions can vary from run to run by as much as 3%. Moreover, when a specimen sample produces less than the standard amount of $CO_2$ required for this process, "dead" $CO_2$ (that is, $^{14}C$-free $CO_2$) has to be added to the sample to make it up to a standard volume.

Further improvements to the above described methods were described by Leaney et al. in their paper, "New developments for the direct $CO_2$ absorbtion method for radiocarbon analysis" in Quaternary Geotechnology/Quaternary Science Review, vol. 13, 1994, pp. 171-178. Their main contribution to the method was to add a plastic bladder to hold the gas sample, and a circulation pump to repeatedly pass the gas through the cocktail by bubbling until saturation is achieved. The method is more efficient, requiring a smaller $CO_2$ excess and it more accurately ensures saturation, and hence the reproducibility of the amount of $CO_2$ absorbed. This may obviate the need to measure the amount of $CO_2$ absorbed in every sample, which is, at best, an imprecise procedure.

However, various factors complicate the method of Leaney et al. As the gaseous $CO_2$ is repeatedly passed through the absorbent cocktail, a significant amount of vapor from the cocktail is entrained in the gas, and must be collected in a moisture trap. This requires the cocktail from the bubbler to be transferred to the moisture trap after absorption, whence the combined amount is transferred into a scintillation counting vial. Furthermore, in Leaney's method, a carrier gas must be added when pressure in the supply vessel drops, and dead $CO_2$ must be added to samples smaller than the standard amount. Furthermore, the apparatus must be thoroughly cleaned, for example with a solvent before the next sample is produced.

Variants of the methods described above are presently in use in various laboratories worldwide, so that a typical current radiocarbon analysis would entail the following.

First, a sample is extracted from the specimen. One or more representative samples are extracted from the specimen for examination. The specimen could entail bone, charcoal, wood etc. for archaeological dating; carbonate, peat etc. for environmental studies; or a carbonate precipitate extracted from water for hydrological investigations.

Second, gaseous $CO_2$ is generated from the sample. The purpose of this step is to free the carbon from the sample and extract it in gaseous form for use in later steps. For this step, therefore, the sample, if not already in a gaseous form, is converted by a suitable process into carbon dioxide ($CO_2$) gas. Organic carbon-containing materials are combusted; inorganic carbon-containing samples (carbonates) are treated with acid. The resulting $CO_2$ is then purified of nitrogenous and sulphurous impurities, of air, and dried in an appropriate gas transfer line.

Third, the carbon dioxide is converted into a form suitable for $^{14}C$ counting. The $CO_2$ gas may be synthesized into benzene through a series of chemical steps. The benzene is mixed with an organic liquid scintillation cocktail suitable for counting in a liquid scintillation spectrometer. Alternatively, in the method described by Qureshi and Aravena (and modified by Leaney), the $CO_2$ may be absorbed into an alkaline absorbent cocktail for counting by scintillation spectrometer. The components of this cocktail are commercially available. The absorbent may be Carbosorb®, and the scintillation cocktail may be Permafluor E®—both by Packard Instrument Co., Meriden, Conn. A typical low-level liquid scintillation spectrometer is the Packard TriCarb® 2770, also by Packard Intrument Co. The vial containing the absorbed sample/scintillation cocktail mixture is placed in the spectrometer, and the scintillations caused by the $^{14}C$ decays are recorded.

However, there are drawbacks to the current standard technology that can be summarized as follows. 1) Because the amount of $CO_2$ gas that will actually be absorbed cannot be assessed beforehand, the method must rely either on measuring the mass of $CO_2$ in the cocktail after it has been absorbed, or on replicating conditions (such as temperature) exactly, so that the same amount of $CO_2$ is absorbed every time. 2) Saturating the cocktail requires either that some of the gas sample must flow to waste, or that the sample must be repeatedly re-circulated. 3) To ensure adequate transport of the $CO_2$ from a supply vessel at low pressure, an inert carrier gas such as nitrogen must be added. 4) The step of bubbling gaseous $CO_2$ through the cocktail is cumbersome. Vapour from the cocktail is entrained in the gas stream, adding to inaccuracies in assessing sample amounts. 5) The cocktail with absorbed $CO_2$ (carbamate) must be transferred from the preparation line to a counting vial. Because the liquid has become rather viscous, the entire amount cannot be readily transferred, leading to inaccuracy. 6) The preparation line must be thoroughly cleaned after each sample in order to avoid cross-contamination (memory effect). 7) When the amount of $CO_2$ derived from the test sample is less than the amount required to saturate the cocktail, "dead" $CO_2$ must be added in known proportion. This leads to inaccuracies because it depends on two pressure measurements: that of the sample and that of the mixture.

Thus, a need exists for an improved apparatus and method for preparing samples for radiocarbon dating that will simplify the pre-existing methodology, increase the efficiency of transferring sample gas into a useful counting cocktail, and increase the accuracy of assessing the amount of sample gas transferred. It is believed that the present invention addresses these and other needs.

SUMMARY OF THE INVENTION

The present invention is directed to establishing a simple, fast, reliable and accurate method for the preparation of a scintillation cocktail for the measurement of the radiocarbon content of $CO_2$ samples in a liquid scintillation spectrometer.

As with the earlier methods described above, the present invention relies on the absorption of $CO_2$ derived from carbon samples to be investigated, but differs from those methods in a number of significant ways.

In general terms, in a preferred method for preparing a sample containing $CO_2$ for analysis by a scintillation spectrometer, a gas transfer apparatus is provided, allowing a sample of $CO_2$ to be introduced into the apparatus where it is initially held in a vessel of known volume, and where the pressure and temperature of the $CO_2$ may be measured. From these measurements, the mass of the $CO_2$ sample may be determined according to the well known relationship between the mass of a gas and its volume, temperature, and pressure. An absorbent is provided in a vial, preferably one of the commercially obtainable absorbents. The mass of absorbent is selected so that it is sufficient to absorb the entire sample of $CO_2$ in the vessel. The $CO_2$ sample is then introduced into the absorbent, allowing substantially the whole of the sample to be absorbed by the absorbent, so that absorption is completed in the vial without the absorbent becoming saturated.

In a preferred embodiment, the introduction of the $CO_2$ into the absorbent from the vessel may be achieved by first freezing substantially all of the $CO_2$ into a trap, then isolating the trap from the vessel. Thereafter, the frozen $CO_2$ in the trap is sublimated, and the resulting gaseous $CO_2$ is allowed to flow into contact with the absorbent in the vial. Absorption is facilitated by cooling and shaking the vial.

In an alternative embodiment, the introduction of the $CO_2$ sample into the absorbent may be achieved by selecting the vessel to be, in effect, a bellows of known volume, capable of mechanically forcing the $CO_2$ into the vial where it is absorbed by the absorbent. Further alternatively, the vessel of known volume may be selected to include a pump, capable of evacuating the contents of the vessel into the vial under pressure.

Once the $CO_2$ sample has been entirely absorbed, the vial is removed and a quantity of scintillation cocktail is introduced into the vial. The vial is inserted into a scintillation spectrometer for analysis. The apparatus is ready to receive the next sample.

Advantages of this method over the prior art, as described above, are apparent. The $CO_2$ absorption proceeds within the vial, which contains the absorbent and is attached to the gas transfer apparatus. The gas transfer apparatus therefore does not come into contact with the absorbent and does not require meticulous cleaning between samples. The gas is absorbed under static conditions, that is, it is not bubbled through the liquid absorber, thus preventing vapor loss. No carrier gas such as nitrogen is required to transport the $CO_2$ when the pressure in the supply vessel falls. The amount of $CO_2$ that is to be absorbed is measured by manometer prior to absorption, by recording its pressure and temperature in the vessel of known volume, typically a 1 litre bulb. This manometric measurement is typically accurate to about 0.3%.

It should be noted that, in the described method, the absorption process is not taken to saturation of the liquid absorbent, but is limited by the fixed amount of $CO_2$ available for absorption. Although this aspect sacrifices a degree of sensitivity (because somewhat less sample $CO_2$ is taken up by the absorbent than in the prior method), it has been found that the sensitivity gained by the other advantages of the method compensate for the loss of sensitivity arising from this aspect. The various aspects of the method allow for the construction of an apparatus which can be partially automated and commercialized as an important interface between commercial liquid scintillation analysers, and those requiring their use for the measurement of radiocarbon in $CO_2$ for a variety of applications.

These and other advantages of the invention will become more apparent from the following detailed description thereof and the accompanying exemplary drawings.

DETAILED DESCRIPTION OF THE PREFERRED EMBODIMENTS

Figure 1:
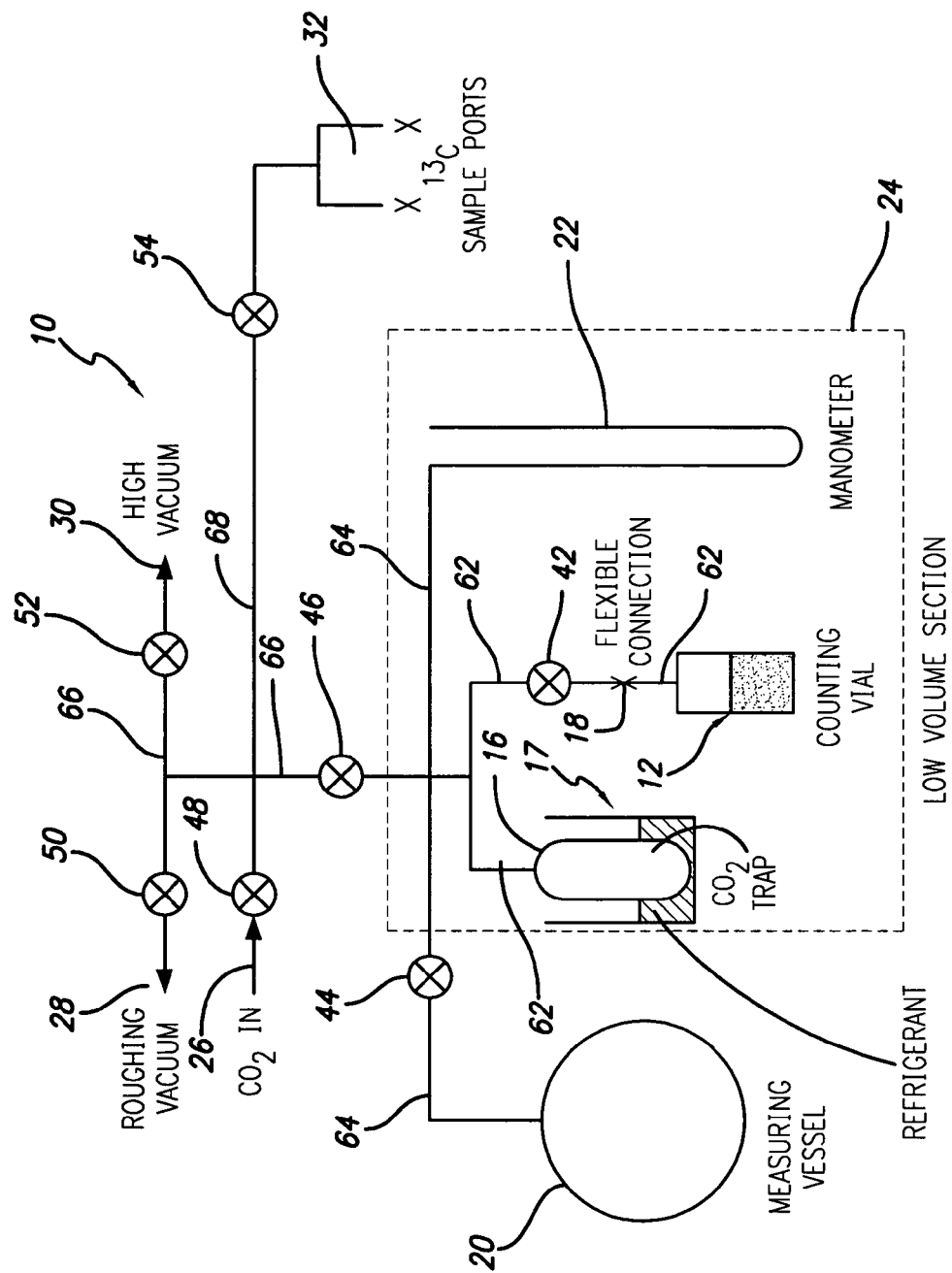
FIG. 1 is a schematic representation of one embodiment of an apparatus suitable for use in the present invention, showing features of the invention.

With reference to FIG. 1 an apparatus, generally referred to by the numeral 10, and method according to a preferred embodiment of the present invention, is described. In general terms, the apparatus is made up of a number of interconnected systems that include collection systems, storage systems, measuring systems, input systems, evacuation systems, and sampling systems. The different systems are interconnected by conduit lines, and isolatable from each other by a plurality of valves.

The terminal point of the apparatus 10 is a collection system preferably in the form of a vial 12 suitable for holding a liquid absorbent capable of absorbing amounts of gaseous $CO_2$ introduced into the vial, and a scintillation cocktail. Preferably, the vial 12 is a standard 20 ml low-potassium glass liquid scintillation counting vial, with cap removed. It is pressed onto a vacuum-tight connection with the line 62 joining to the balance of the apparatus. A flexible joint 18, preferably a short length of tygon thick-walled hosing enabling the vial to be gently shaken, connects the vial with the balance of the apparatus 10.

Feeding the vial 12 through line 62 is an intermediate storage system for acting as a $CO_2$ trap 16, which preferably may be a vertically mounted 10 ml Pyrex glass tube, isolatable from the vial by a valve 42. The trap 16 is adapted to be enclosed by a refrigerant 17, preferably a bath of liquid nitrogen, to freeze the gaseous $CO_2$ introduced into the trap.

Feeding the trap 16 through line 64 is a measuring vessel 20, preferably in the form of a 1 liter Pyrex glass bulb, for receiving a gaseous $CO_2$ sample. A manometer 22 connects to the measuring vessel 20, through line 64, for taking pressure measurements within the measuring vessel, whereby the mass of a gaseous $CO_2$ sample inside the measuring vessel may be determined according to the well known relationship between the mass of a gas sample and its volume, temperature, and pressure. The vial 12, the $CO_2$ trap 16, and the manometer 22 are collectively referred to as the low volume section 24, which preferably does not exceed 60 ml in cumulative total volume. The measuring vessel 20 is isolatable from the low volume section 24 by a valve 44. The low volume section is further isolatable from input, extraction, and sampling systems of the apparatus 10 by an isolation valve 46.

Feeding into the apparatus through line 66, and isolatable by a valve 48, is a supply system 26 adapted to introduce into the apparatus a gaseous $CO_2$ sample, obtained from a specimen whose $^{14}C$ level is to be determined by the liquid scintillation method, the sample having been purified of nitrogen and sulphur oxides and air, and dried according to known standard procedures.

A roughing vacuum system 28, isolatable by valve 50 on line 66, is adapted to apply an initial vacuum of around $10^{-2}$ torr to the apparatus 10. A high vacuum system 30, isolatable by valve 52 on line 66, is adapted to improve the vacuum to about $10^{-4}$ torr.

Finally, a sample extraction system in the form of a sample port 32 may be configured to feed from the apparatus 10 through line 68 under control of an isolation valve 54. Preferably, the sample port 32 may be a pair of hypodermic needles adapted to be pushed into serum caps on 5 ml glass vials into which quanta of the $CO_2$ sample in the apparatus may be fed for subsequent mass spectrometry, an aspect which is collateral to the method of the present invention.

All the connection lines described herein and exemplified in FIG. 1 are preferably Pyrex glass tubing, but in a more robust commercial embodiment may be stainless steel.

In use, the above described apparatus may be used according to a preferred method, as follows.

The apparatus is evacuated by the roughing vacuum system 28 to a pressure of about $10^{-2}$ torr. The high vacuum system 30 then increases the vacuum to about $10^{-4}$ torr.

A sample of gaseous $CO_2$, derived from a specimen whose level of $^{14}C$ is to be determined, is introduced into the apparatus 10 from the supply system 26. In a preferred embodiment, the $CO_2$ sample may be held by the supply system in a frozen state prior to introduction into the apparatus. Upon introduction, it is warmed to ambient temperature whereupon it sublimates and flows via lines 66, 64 into the measuring vessel 20. The pressure in the measuring vessel is then carefully measured using the manometer 22. From its volume, temperature, and pressure, the mass of the gaseous $CO_2$ sample in the measuring vessel 20 can be determined. The pressure in the measuring vessel, and indeed in the entire apparatus, is preferably set to operate (when not at a vacuum) below ambient atmospheric pressure to keep vacuum joints and stopcocks from being forced open or glass volumes from exploding. For example, at 1600 meters above mean sea level the ambient pressure is about 625 torr. Accordingly, at such altitude the apparatus 10 may preferably be set to operate at a maximum of 610 torr. In this particular example, 610 torr would be taken to be the "standard" amount.

As a collateral step, when maximum pressure is reached (either the standard 610 torr or a lesser pressure dictated by the available amount of sample gas) sample port valve 54 may be opened to connect the sample ports 32 to the transfer line, and two small quanta of the $CO_2$ sample gas may be collected in from the measuring vessel to pre-evacuated detachable ampoules for carbon-13 mass spectrometry analysis. As will be appreciated by one of ordinary skill, Carbon-13 values are usually required to interpret carbon-14 results. These samples may therefore be required during the subsequent interpretation process, which is not described herein.

After the pressure and temperature of the $CO_2$ sample in the measuring vessel 20 is determined, the measuring vessel may be isolated from the apparatus by closing valve 44. Any excess gas in the balance of the apparatus may be either pumped to waste through valve 50 to roughing vacuum 28, or may be returned through valve 48 to the supply line 26 by freezing under liquid nitrogen.

At this point, a quantity of a liquid absorbent, preferably about 10 ml of Carbosorb®E+, may be pipetted into the counting vial 12. The vial 12 may then be evacuated by roughing vacuum 28 for a second or two by briefly opening valves 42, 46, 50 to remove air. The line is again evacuated by high vacuum system 30 (opening valve 52). It will be appreciated that the $CO_2$ trap 16 will also be evacuated in this process. Valve 42 is then closed to isolate the counting vial 12 from the trap 16.

At this point, $CO_2$ trap 16 may be immersed in the refrigerant 17, which preferably is liquid nitrogen. The line 64, 62 connecting the measuring vessel 20 to the trap 16 may then be opened (with valve 46 closed, valve 44 is opened). The $CO_2$ in measuring volume 20 is allowed to flow from the gaseous environment of the measuring volume 20 to be frozen into the trap 16. The flow of $CO_2$ is allowed to proceed until substantially all of the $CO_2$ has been frozen. This stage will be determined to have been reached when the manometer 22 registers less than 1 torr pressure in the measuring vessel. Whereupon, the trap 16 is isolated from the measuring volume 20 by closing valve 44.

Following this step, trap 16 with its contents of frozen $CO_2$ may be briefly evacuated to a high vacuum, to remove any traces of air which may have entered, whereafter the small volume section 24 is isolated from the rest of the apparatus by closing valve 46. Valve 44 also remains closed, isolating the small volume section from the measuring vessel 20.

At this point, the content of the vial 12 is exposed to the content of the $CO_2$ trap 16 by opening valve 42. The trap 16 is gently warmed, allowing the frozen $CO_2$ to sublime, whilst the vial 12 is immersed in a water bath and gently shaken to facilitate absorption of the gaseous $CO_2$.

Absorption of the $CO_2$ may be allowed to continue until the pressure in the first and second containers has fallen to less than 10% of the pressure originally measured in the much larger measuring vessel 20. An important aspect of the invention is that the combined volume of the trap 16, the vial 12, their connecting conduit 62 and the pressure measuring manometer 22 to which they are connected, is preferably less than about 5% of the volume of the measuring vessel 20. This aspect has the result that, when the pressure during absorption has fallen to less than 10% of the pressure the sample registered in the measuring vessel 20, substantially all of the $CO_2$ from the sample will have been absorbed into the liquid absorbent because there is no large space in which gaseous $CO_2$ can remain after absorption, and the low pressure means that any $CO_2$ that does remain in the small volume section 24 after absorption does not constitute a large mass.

Thus, following this principle in the present example, the pressure in the small volume section 24 is monitored by the manometer 22 to remain between about 300 to 400 torr during the absorption process. Under these conditions, gaseous $CO_2$ flows to the vial 12 where it is absorbed into the liquid absorbent contents. The relatively small volume (about 60 ml) of the small volume section 24 allows the pressure to be maintained at between 300 and 400 torr throughout almost the entire process under which $CO_2$ is transferred to the vial. When all the $CO_2$ has sublimated, shaking of the vial continues until the pressure drops to about 40 torr, which has been found to be the typically encountered residual pressure under these conditions. It may be noted that, as the $CO_2$ pressure drops near the end of the absorption process, it diffuses less readily through a "blanket" of ammonia gas exuded by and overlying the liquid absorbent, as well as traces of air entrained by the $CO_2$ into the vial. However, it will be appreciated by one of ordinary skill in the art that, because the pressure of the residual gas (about 40 torr) is contained in a volume of only about 60 ml, the residual gas constitutes about 0.4% of the maximum total of the original available gaseous $CO_2$ sample that was initially introduced into the 1 liter measuring vessel 20—a negligible amount. It will be appreciated that, if the volume of the small volume section 24 is known, and the post absorption temperature and pressure of the $CO_2$ above the absorbent is known, the amount of $CO_2$ from the original sample not absorbed may be approximately calculated, and a correction made to account for the non-absorption. Under these circumstances, it may be said that the $CO_2$ has been substantially entirely absorbed. This residual pressure of 40 torr has been found to be reproducible to about 10 torr from sample to sample. It will be appreciated by one of ordinary skill that such reproducibility permits the inference that the volume of gaseous $CO_2$ actually absorbed using this method from sample to sample to be to within a range of difference of 0.2%, which implies a reproducibility of 99.8%.

It is important to note that the described method is not designed to saturate the alkaline absorbent in the vial 12 with $CO_2$, for, if the absorbent becomes saturated, an unknown and perhaps significant portion of the known mass of $CO_2$ would be left in the gaseous state above the absorbent. This could render the results of the procedure significantly unreliable, because the scintillation count would be based on an incorrectly computed mass of absorbed $CO_2$. Accordingly, to avoid this result, the mass of $CO_2$ and the amount of liquid absorbent should preferably be estimated beforehand to produce about 85% saturation of the absorbent, leaving a safety margin of about 15%. This may be called the standard amount, which would apply also to reference standards. Absorption of an amounts of $CO_2$ considerably less than this, as low as 40% saturation, can be readily absorbed without dilution. It will be appreciated that the amount of $CO_2$ absorbed does not significantly affect the final outcome of the procedure. Small differences in the scintillation counting characteristics can be compensated for by quench correction, a standard procedure in this technique. However, it may be noted that as the amount of absorbed $CO_2$ is reduced, the noise (background count) to signal ratio of the scintillation measurements increases, and may reduce the resulting precision. However, it will also be appreciated that, by terminating the absorption process well before saturation, the final exponentially lengthy stages of absorption, requiring the addition of a carrier gas, are avoided, thus significantly speeding up the entire process.

An additional aspect of carrying out the method is that, when the $CO_2$ sample measures less than the 610 torr standard pressure ($p_{max}$) in measuring vessel 20, the pressure ($p_{meas}$) is recorded in order to normalize the sample amount to the standard. The normalization is simply by the factor $p_{max}/p_{meas}$.

Once the $CO_2$ has been entirely transferred from its frozen state in the trap 16 to an absorbed state in the vial 12, the vial is isolated from the balance of the apparatus by closing valve 42. The vial 12 is then removed from the line, an amount of scintillation cocktail, preferably about 10 ml Permafluor®E+, is pipetted into the vial which is then shaken, capped and the required information written on the cap. The vial is now ready for placement in a scintillation spectrometer to be analyzed for the level of carbon-14. As discussed above, this value can then be translated into the age of the specimen from which the $CO_2$ sample was generated.

The line is immediately ready to handle the next sample after pumping to high vacuum.

Figure 2:
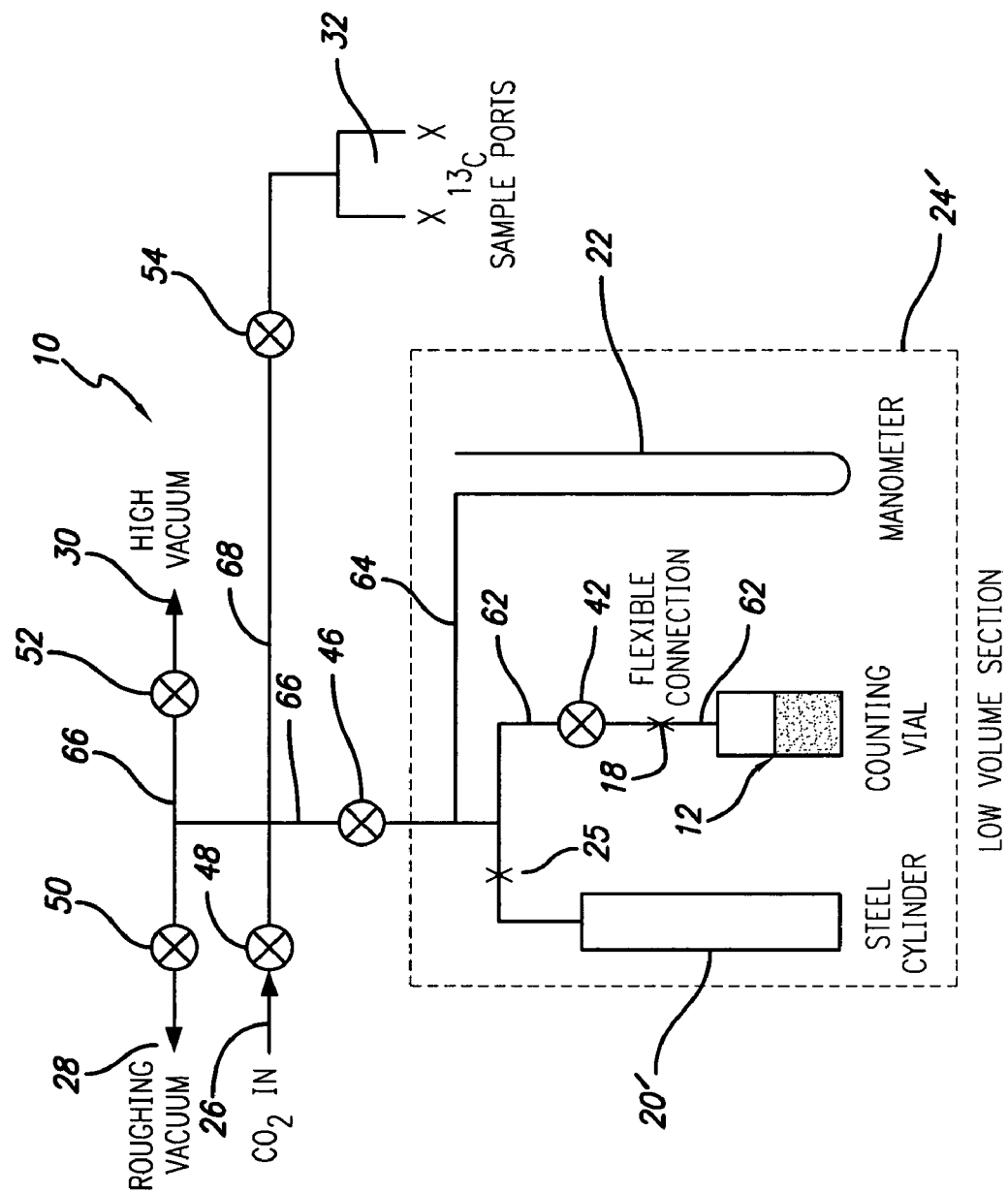
FIG. 2 is a schematic representation of an alternative embodiment of an apparatus suitable for use in the present invention, showing features of the invention.

In an alternative embodiment, exemplified in FIG. 2, the measuring vessel 20 in the form of a glass bulb may be replaced by an alternative measuring vessel having the form of a vertical stainless steel cylinder 20', preferably about 100 ml in volume, fitted with a transducer and an automated release/pressure control servo valve 25 feeding into the vial 12. The $CO_2$ trap in this embodiment is eliminated. An amount of $CO_2$ gas may be transferred into the cylinder 20' by freezing, whereafter the $CO_2$ may be thawed and the temperature and pressure within the cylinder 20' recorded to determine the mass of $CO_2$ within, using the known relationship between mass, pressure, temperature, and volume. The cylinder 20' may be warmed and the $CO_2$ gas allowed to flow into the vial 12 with absorbent, via the servo valve 25 which limits the pressure in the vial 12 to preferably about 400 torr. When the pressure in the cylinder 20' falls below 400 torr, the servo valve 25 remains open until the final approximately 40 torr is reached. It will be appreciated that the small volume section 24' (FIG. 2) will in this example be approximately 130 ml instead of approximately 60 ml, and accordingly the unabsorbed $CO_2$ loss will be greater than in the previous embodiment. However, it will be appreciated that, at this stage, the $CO_2$ will have been substantially entirely absorbed by the absorbent. Whereupon the vial 12 may be removed, and the procedure continued as before, using a scintillation spectrometer to analyze the sample in the vial.

Figure 3:
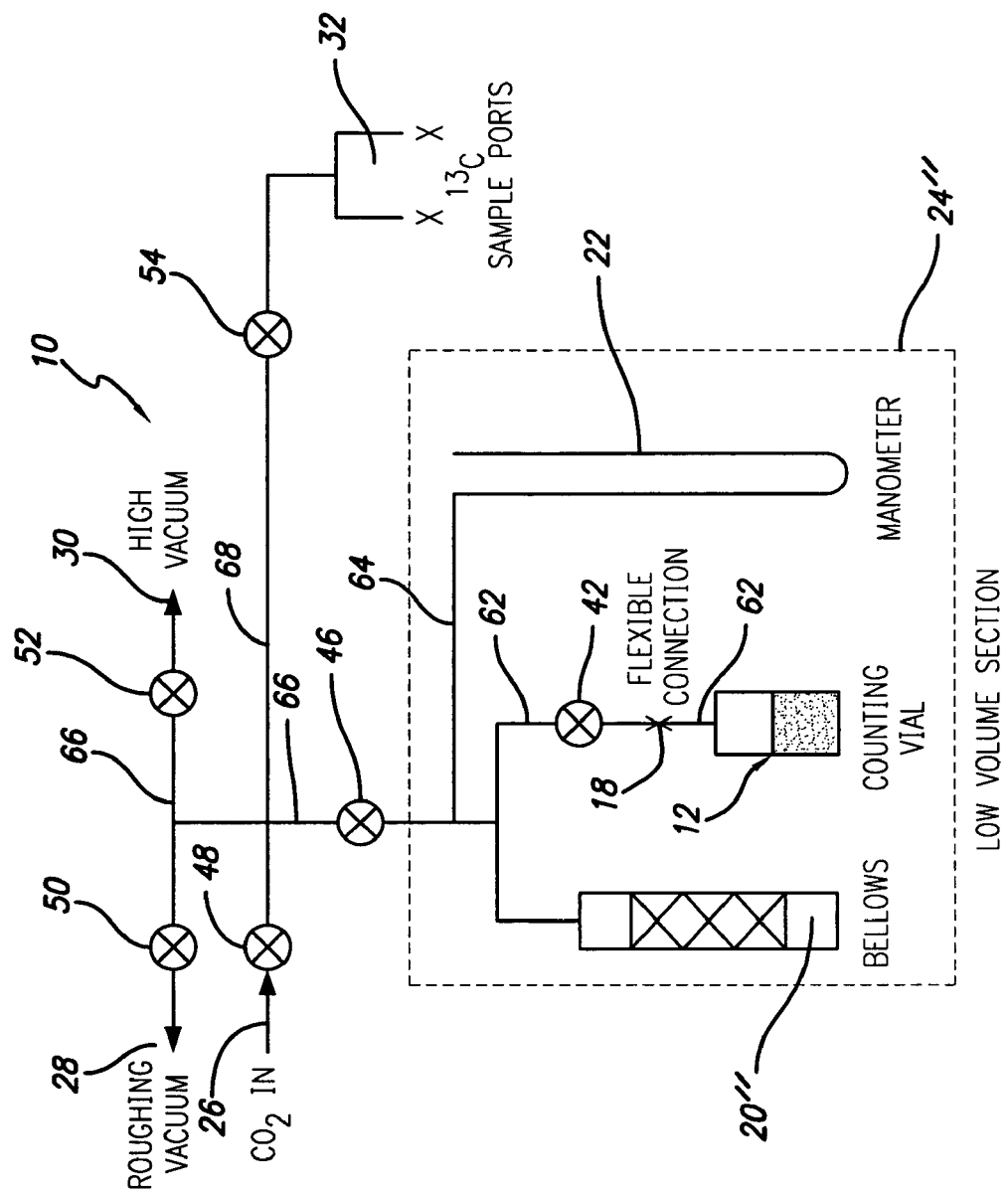
FIG. 3 is a schematic representation of a further alternative embodiment of an apparatus suitable for use in the present invention, showing features of the invention.

In yet a further alternative embodiment, exemplified in FIG. 3, the measuring vessel 20 may be replaced by an alternative measuring vessel having the form of a stainless steel bellows 20" of approximately 1 liter volume which can be compressed to approximately say 100 ml or less by a servo motor (not shown). The gas from the supply line is frozen into a small (approximately 20 ml) trap (not shown) and fed into the pre-evacuated bellows 20" to just below atmospheric pressure. The manometer 22 measures the pressure in the bellows, hence the mass of gas may be determined if the temperature is known. The bellows 20" may be opened to the absorbent in the vial 12. As the pressure drops, it may be maintained at about 400 torr by squeezing the bellows with the servo motor. Eventually, the bellows 20" is completely compressed until the pressure drops to about 40 torr. It will be appreciated that, at this stage, the $CO_2$ will have been substantially entirely absorbed by the absorbent. Whereupon the vial 12 removed, and the procedure continued as before, using a scintillation spectrometer to analyze the sample.

While a particular form of the invention has been illustrated and described, it will also be apparent to those skilled in the art that various modifications can be made without departing from the spirit and scope of the invention. Accordingly, it is not intended that the invention be limited except by the appended claims.

We claim:

1. A method of preparing a quantity of gaseous carbon dioxide for analysis by a scintillation spectrometer, comprising:
   providing a first container of known volume;
   introducing a sample of gaseous carbon dioxide into the first container under known temperature and pressure, whereby the mass of the sample of carbon dioxide is quantifiable;
   providing a second container for acting as a trap;
   connecting the first container to the second container via a valve controlled conduit;
   volumetrically isolating the interconnected first container and second container;
   causing the sample of carbon dioxide to become entrapped in the second container by freezing;
   providing an absorbent in a third container in a mass sufficient to absorb more than the whole of the sample of carbon dioxide;
   closing the connection between the first container and the second container;
   connecting the second container to the third container via the valve controlled conduit to form a combined volume;
   volumetrically isolating the interconnected second container and third container;
   causing the sample of carbon dioxide in the second container to sublime;
   introducing the sample of carbon dioxide into the absorbent while the combined volume of the second container and third container is volumetrically isolated, whereby the carbon dioxide is introduced into the absorbent under static conditions;
   causing the sample of carbon dioxide to be absorbed by the absorbent.

2. The method of claim 1, further comprising inserting the third container with the absorbent into a scintillation spectrometer for analysis after the sample of carbon dioxide is absorbed.

3. The method of claim 1, wherein introducing the sample of carbon dioxide into the absorbent includes shaking the absorbent.

4. The method of claim 1, wherein introducing the sample of carbon dioxide into the absorbent includes cooling the absorbent.

5. The method of claim 4, wherein cooling includes using a liquid bath as a coolant.

6. The method of claim 5, wherein using a liquid bath includes using water.

7. The method of claim 1, wherein providing an absorbent includes providing an absorbent in liquid form capable of absorbing gaseous carbon dioxide by converting it to a carbamate.

8. The method of claim 1, further including introducing a quantity of a scintillation-promoting substance to the absorbent after absorption has been completed.

9. An apparatus for preparing a predetermined mass of carbon dioxide for analysis by a scintillation spectrometer, comprising:
- a vessel for holding the predetermined mass of carbon dioxide;
- a trap for freezing the carbon dioxide, the trap being connectable to the vessel by a valve-controlled conduit, the vessel and trap being volumetrically isolatable when interconnected;
- a vial for holding a liquid absorbent, the vial being connectable to the trap by the valve-controlled conduit, the trap and vial being volumetrically isolatable when interconnected;
- wherein, the frozen carbon dioxide in said trap is sublimated, and the resulting gaseous carbon dioxide flows into contact with the absorbent in said vial;
- a manometer connectable selectively by the valve-controlled conduit to the vessel and the trap when the vessel and trap are interconnected and volumetrically isolated, and also connectable selectively to the vial and the trap when the vial and trap are interconnected and volumetrically isolated;
- wherein the combined volume of the trap, the vial, the manometer, and the conduit does not exceed about 5% of the volume of the vessel.

10. The apparatus of claim 9, further comprising means to agitate the contents of the vial.

11. The apparatus of claim 9, further comprising means to apply a vacuum of varying degree to the vessel, the trap, and the vial.

12. The apparatus of claim 9, wherein the vial is made of low-potassium glass.

13. The apparatus of claim 9, wherein the conduit connecting the vial to the trap is flexible.

14. An apparatus for preparing a predetermined mass of carbon dioxide for analysis by a scintillation spectrometer, comprising:
- a vessel for holding the predetermined mass of carbon dioxide;
- a vial for holding a liquid absorbent, the vial being connectable to the vessel by a valve-controlled conduit, the vessel and vial being volumetrically isolatable when interconnected;
- means for causing the transfer of the carbon dioxide from the vessel and into the vial, so that the carbon dioxide is thereby caused to be absorbed into the absorbent under static conditions;
- wherein the means for causing the transfer of the carbon dioxide includes means for first freezing, and then sublimating, the carbon dioxide.

15. The apparatus of claim 14, further including a manometer connectable selectively by the valve-controlled conduit to the vessel and the vial when the vessel and the vial are interconnected and volumetrically isolated.

16. The apparatus of claim 14, wherein the means for causing the transfer of the carbon dioxide includes a bellows for squeezing the carbon dioxide into the vial.

17. The method of claim 1, wherein causing the sample of carbon dioxide to be absorbed by the absorbent includes measuring the extent of absorption during absorption.

18. The method of claim 17, wherein measuring the extent of absorption includes using a manometer.

19. The method of claim 1, wherein causing the sample of carbon dioxide to be absorbed by the absorbent includes causing substantially all of the sample to be absorbed.

20. The method of claim 1, wherein causing the sample of carbon dioxide to become entrapped in the second container by freezing includes measuring the extent of freezing during freezing.

21. The method of claim 20, wherein measuring the extent of freezing during freezing includes using a manometer.

22. A method of preparing a quantity of gaseous carbon dioxide for analysis by a scintillation spectrometer, comprising:
- providing a vessel of known volume;
- introducing a sample of gaseous carbon dioxide into the vessel under known temperature and pressure, whereby the mass of the sample of carbon dioxide is quantifiable;
- providing an absorbent in a vial, in a mass sufficient to absorb more than the whole of the sample of carbon dioxide;
- connecting the vessel to the vial via a conduit to form a combined volume;
- volumetrically isolating the interconnected vessel and vial;
- introducing the sample of carbon dioxide into the absorbent while the combined volume of the vessel and the vial is volumetrically isolated, whereby the carbon dioxide is introduced into the absorbent under static conditions;
- and whereby said introducing said sample into the absorbent from the vessel is achieved by first freezing substantially all of the carbon dioxide into a trap, then isolating the trap from the vessel, thereafter sublimating the frozen carbon dioxide in the trap, and flowing the resulting gaseous carbon dioxide into contact with the absorbent in the vial;
- causing the sample of carbon dioxide to be absorbed by the absorbent.

23. The method of claim 22, wherein introducing the sample of carbon dioxide into the absorbent includes evacuating the carbon dioxide from the vessel into the vial with a motorized pump.

24. The method of claim 22, wherein the vessel is a bellows, capable of being squeezed to reduce its volume, and further wherein introducing the sample of carbon dioxide into the absorbent includes evacuating the carbon dioxide from the vessel into the vial by squeezing the bellows.

25. The method of claim 22, wherein causing the sample of carbon dioxide to be absorbed by the absorbent includes measuring the extent of absorption during absorption.

26. The method of claim 22, wherein measuring the extent of absorption includes using a manometer.

* * * * *